United States Patent [19]

Billings

[11] 4,113,784

[45] Sep. 12, 1978

[54] CONVERSION OF ORGANIC SULFIDES TO CORRESPONDING SULFOXIDES

[75] Inventor: William G. Billings, Bartlesville, Okla.

[73] Assignee: Phillips Petroleum Company, Bartlesville, Okla.

[21] Appl. No.: 811,426

[22] Filed: Jun. 29, 1977

[51] Int. Cl.$^2$ .................................... C07C 147/14
[52] U.S. Cl. .................. 260/607 AR; 260/607 AL
[58] Field of Search ..... 260/607 A, 607 AR, 607 AL

[56] References Cited

U.S. PATENT DOCUMENTS

| | | | |
|---|---|---|---|
| 2,787,595 | 4/1957 | Webb | 252/138 |
| 2,859,248 | 11/1958 | Louthan | 260/607 |
| 2,935,533 | 5/1960 | Hubenett | 260/607 |
| 3,708,542 | 1/1973 | Douchet et al. | 260/607 A |
| 3,808,112 | 4/1974 | Thibault et al. | 204/79 |

OTHER PUBLICATIONS

J. Org. Chem., 40(21), 3152-4, (1975).
J. Org. Chem., 28, 3246-7, (1963).
J. Org. Chem., 23(7), 2028-9, (1958).

Primary Examiner—Lewis Gotts
Assistant Examiner—Molly C. Eakin

[57] ABSTRACT

Suitable organic sulfides are converted to the corresponding organic sulfoxides by contacting with at least one suitable hydrocarbyl sulfoxide, a protonic acid, and a suitable metal promoter. Alternatively, if hydrogen chloride is the protonic acid, graphite or suitable metal promoters can be employed.

24 Claims, No Drawings

CONVERSION OF ORGANIC SULFIDES TO CORRESPONDING SULFOXIDES

This invention concerns the production of organic sulfoxides. In another aspect this invention relates to the oxidation of organic sulfides by hydrocarbylsulfoxides.

Searles and Hays in the *Journal of Organic Chemistry*, 23(7), 2028–2029 (1958), reported that dimethyl sulfoxide would oxidize n-propyl, n-butyl, and tetramethylene sulfides to the corresponding sulfoxides. The conditions involved heating the sulfide with a 50 percent molar excess of dimethyl sulfoxide at 160°–175° C for 8–12 hours to obtain yields in the range of 55 to 59 percent.

More recently Hall and Bargar in the *Journal of Organic Chemistry*, 40(21), 3152–3154 (1975) reported the oxidation of n-butyl sulfide, isobutylsulfide, benzyl sulfide, and cyclohexylsulfide with dimethyl sulfoxide in the presence of hydrogen chloride to yield the corresponding sulfoxides.

It ws also reported that no disulfoxide was produced when 2,5-dithiohexane was heated with dimethyl sulfoxide; but that upon the addition of small amounts of hydrogen chloride the corresponding disulfoxide was obtained in good yield. The hydrogen chloride was thus viewed by those authors as a catalyst. Other substances there reported as being "catalysts" were bromine, hydrogen bromide, and bromosuccinimide. Iodine, hydrogen iodide, hydrogen fluoride, nitric acid, sulfuric acid, and boron trifluoride were reported as having little or no catalytic effect.

Recently it has been discovered that in reactions of organic sulfides with dimethyl sulfoxide the amount of hydrogen chloride affects the rate of yield of corresponding sulfoxide. The present invention is based upon the discovery that the yield of the desired sulfoxide can be increased by employing a catalytic amount of a metal promoter or graphite in combination with hydrogen chloride in such reactions. In addition, the present invention is based upon the discovery that protonic acids in general when employed with a chloride-containing metal promoter will catalyze the conversion of organic sulfides to the corresponding sulfoxides by oxidation with sulfoxides.

Accordingly, an object of the present invention is to provide an improved method for the oxidation of organic sulfides by sulfoxides.

Other objects, advantages, and benefits of the present invention will be apparent from this disclosure and the appended claims.

The organic sulfides which can be employed as reactants in accordance with this invention are those organic sulfides having at least one hydrogen on at least one of the two bonded to the sulfur. Such organic sulfides include those of the formula:

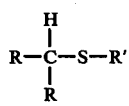

wherein each R is individually selected from the group consisting of hydrogen, hydrocarbyl radicals, and hydrocarbyl radicals substituted with groups which don't interfere with the reaction or where the two R groups as above defined are joined to form a hydrocarbyl carbocyclic ring or a carbocyclic ring substituted with groups which don't interfere with the reaction and wherein R' is a hydrocarbyl radical or a hydrocarbyl radical substituted with groups which don't interfere with the reaction. Examples of subsituents which would not be expected to interfere with the reaction include —OH,

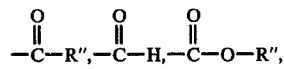

— R″ — O — R″, — O — R″, halogens, etc., where R″ is a hydrocarbyl radical having from 1 to 12 carbon atoms. The organic sulfides now preferred as reactants in the present invention are those were

and —R' each contain 1 to 12 carbon atoms,

is selected from the group consisting of alkyl, cycloalkyl, and aralkyl groups and —R' is selected from the group consisting of alkyl, cycloalkyl, aralykyl, alkaryl, and aryl groups. Typical examples of sulfides that can be employed as reactants in this invention include, dimethyl sulfide, diethyl sulfide, di-n-propyl sulfide, di-n-butyl sulfide, di-isobutyl sulfide, di-n-octyl sulfide, methyl ethyl sulfide, tertiary butyl methyl sulfide, tertirary butyl isobutyl sulfide, tetramethylene sulfide, dicyclohexyl sulfide, methyl cyclohexyl sulfide, dicycloctyl sulfide, methyl phenyl sulfide, methyl benzyl sulfide, dibenzyl sulfide, benzyl phenyl sulfide, tertiary butyl-2-phenyl-1-ethyl sulfide, and n-propyl-o-tolyl sulfide. Mixtures of sulfides can also be employed.

The hydrocarbyl sulfoxides suitable for use in this invention are those of the formula

wherein each A is individually selected from the same or different alkyl radical having from 1 to 12 carbon atoms or wherein the two such A alkyl groups are combined by a bond to form a sulfur-containing cyclic ring containing at least 4 carbons in the cyclic ring. Examples of such hydrocarbyl sulfoxides include dimethyl sulfoxide, diethyl sulfoxide, methyl ethyl sulfoxide, didodecyl sulfoxide, tetramethylene sulfoxide, and mixtures of any two or more thereof.

Sulfide and sulfoxide as above described can be reacted in any proportions which result in the formation of sulfoxide corresponding to the sulfide. Generally, the molar ratio of sulfoxide to sulfide is in the range of about 500:1 to about 1:10. It is preferably for the molar ratio of sulfoxide to sulfide to be in the range of about 20:1 to about 1:1.

Although it is not necessary, it is preferred that the oxidation be conducted in the presence of a diluent. Suitable diluents include any organic liquid that does not have a significant adverse effect on the reaction. Examples of suitable diluents include monohydric alcohols, for example, benzyl alcohol, methanol, ethanol, butanol, and the like; ethers of the type E — O — E' where E and E' may be the same or different alkyl or aryl radicals, for example, diethyl ether, dipropyl ether, di-n-butyl ether, diphenyl ether, and the like; hydrocarbons, for example, benzene, toluene, heptane, hexane, and the like; or mixtures of any two or more diluents of that sort. The preferred diluents are saturated aliphatic monohydric alcohols having 1 to 8 carbon atoms. Any amount of diluent can be employed which does not adversely affect the course of the reaction. Generally the number of moles of diluent is no greater than about 10 times the sum of the moles of organic sulfide and hydrocarbyl sulfoxide and no less than about 0.01 of the sum. Of course, one can by routine experimentation determine other concentrations of sulfide and diluent that are operable. Preferably the number of moles of diluent is no greater than about 6 times the sum of the moles of organic sulfide and hydrocarbyl sulfoxide and no less than about 0.1 of that sum.

When the present invention is conducted employing hydrogen chloride, either hydrochloric acid or hydrogen chloride gas can be employed. The hydrogen chloride can be employed in any amount which provides a suitable yield. It is preferred that the molar ratio of hydrogen chloride to organic sulfide reactant be in the range of about 0.05:1 to about 2.5:1.

In conjunction with the hydrogen chloride, at least a small amount of a suitable metal promoter and/or graphite is employed. The metal promoter and/or graphite is employed in any amount which will provide a rate of sulfoxide production greater than what would be provided if the organic sulfide and hydrocarbyl sulfoxide reactants were contacted in the presence of hydrogen chloride alone. Generally about 0.0001 to about 1.0 mole of metal promoter or graphite per mole of organic sulfide reactant is sufficient to provide such a catalytic effect, preferably about 0.02 to about 0.2 moles of metal promoters or graphite. Suitable metal promoters include any noncovalent metal halides and any covalent metal halides capable of forming coordination compounds and chloroplatinic acid. Examples of suitable metal promoters include lead chloride, zinc chloride, iron chloride, iron bromide, sodium iodide, sodium chloride, lithium chloride, calcium chloride, copper dichloride, bismuth trichloride, antimony pentachloride, boron trifluoride, cadmium chloride, chloroplatinic acid, sodium fluoride mercury dichloride, and mixtures of such. Also, intercalation compounds of such promoters can be employed.

The oxidation of organic sulfides with hydrocarbyl sulfoxides can also be obtained according to the present invention by employing protonic acids other than hydrogen chloride provided a sufficient amount of a suitable chloride-containing metal promoter is also employed. Generally any protonic acid is suitable. Examples of such acids include hydrogen bromide, hydrobromic acid, hydrofluoric acid, sulfuric acid, nitric acid, acetic acid, propionic acid, trichloracetic acid, chlorosulfuric acid, phthalic acid, benzenesulfuric acid, and orthophosphoric acid. Any amount of acid can be employed that is sufficient to provide a yield of the desired sulfoxide. It is preferred that the amount of acid used per mole of organic sulfide reactant be such that it would provide a hydrogen ion concentration in the range of an amount about equivalent to the hydrogen ion concentration provided by 0.05 mole of hydrogen chloride to an amount about equivalent to the hydrogen ion concentration provided by 2.5 moles of hydrogen chloride. The amount of chloride-containing metal promoter employed with such protonic acids is that which will provide a yield of hydrocarbyl sulfoxide greater than what would be provided if the organic sulfide and hydrocarbyl sulfoxide reactants were contacted in the presence of the protonic acid alone.

Generally, about 0.0001 to about 1.0 mole of chloride-containing metal promoter per mole of organic sulfide reactant is sufficient to provide such an effect. Preferably about 0.02 to about 0.2 moles of chloride-containing metal promoter are employed per mole of organic sulfide reactant.

In general, any noncovalent metal chloride or covalent metal chloride capable of forming complex chloride coordination compounds can be employed as the chloride-containing metal promoter. Also chloroplatinic acid can be employed as the chloride-containing metal promoter. Gallium chloride, which is covalent in nature but does not form a complex chloride, was not effective.

Regardless of whether hydrogen chloride or some other protonic acid is employed, the reaction conditions of temperature and pressure are the same. Generally, the temperature of reaction is in the range of from about 18° to about 180° C, preferably in the range of from about 50° to about 80° C. Any suitable pressure conditions can be employed. It is preferred to conduct the reaction at atmospheric pressure. As with other organic reactions, the time of reaction will be dependent upon the temperature and pressure selected and the extent of conversion desired.

The following examples demonstrate the present invention and its significance. The examples are not intended to be construed as limiting the foregoing disclosure.

The reactions described in Examples I–III below were carried out in a quartz reactor equipped with a gas inlet tube, a thermocouple well, a reagent inlet tube, and an exit tube. A control thermocouple, inserted between the walls of the reactor and heater was connected to a thermoelectric temperature control unit. Nitrogen was bubbled through each reaction mixture for about five minutes at a rate of about 100 cc per minute prior to heating. The reaction temperature was recorded in response to the thermocouple.

EXAMPLE I

A series of reactions were conducted employing portions of a stock solution consisting of 20 ml (0.116 moles) di-n-butyl sulfide, 80 ml (1.13 moles) dimethyl sulfoxide, 418 ml (7.17 moles) absolute ethanol and 2 g (0.011 moles) dibenzothiophene. The dibenzothiophene was nonreactive under the conditions employed and was included as a standard for use in subsequent gas-liquid chromatographic (GLC) analysis of the reaction samples. In each run, 20 ml of the stock solution was heated under a nitrogen atmosphere for 2 minutes at about 72° C (161° F) in the presence of 0.41 g of 12 molar hydrochloric acid (equivalent to about 0.005 moles hydrogen chloride). Catalytic amounts of a specified metal promoter or graphite were also employed as indicated below. In these runs, the molar ratio of hydrogen chloride to di-n-butyl sulfide was about 1.1:1. The molar ratio of the sulfoxide to organic sulfide was 9.7:1. The number of moles diluent employed was 5.8 times the sum of the moles of sulfoxide and sulfide employed.

After the reaction period, a sample of each reaction composition was analyzed and the amount of the di-n- butyl sulfide converted to di-n-butyl sulfoxide was determined.

When no metal promoter or graphite was employed in a control run, it was found that 20.6% of the di-n-butyl sulfide was converted to di-n-butyl sulfoxide.

When about 0.001 moles of ferric chloride was added to the reaction mixture, it was found that 28% of the di-n-butyl sulfide was converted to di-n-butyl sulfoxide after the heating period. This represents an increase of 36% over the control run results. The molar ratio of ferric chloride to organic sulfide was about 0.2:1.

When about 0.02 moles of powered graphite was added to the reaction mixture, it was found that 40.9% of the di-n-butyl sulfide was converted to di-n-butyl sulfoxide after the heating period. This represents an increase of about 98% over the control run results. The molar ratio of graphite to organic sulfide was about 0.2:1.

In a duplicate run employing graphite, it was found that the conversion was 25.6%, represents an increase of about 24% over the control run. It was not understood why closer agreement was not achieved. However, in any event, the combination of graphite and hydrochloric acid demonstated an improvement over the results obtained with the use of hydrochloric acid alone.

When about 0.0005 moles of chloroplatinic acid was added to the reaction mixture, it was found that 31.8% of the di-n-butyl sulfide was converted to di-n-butyl sulfoxide after the heating period. This corresponds to an increase of about 54% over the control run results.

In a duplicate run employing chloroplatinic acid, it was found that the conversion was 32.6%, representing an increase of about 58% over the control run results. In both of the runs employing chloroplatinic acid, the molar ratio of chloroplatinic acid to organic sulfide was about 0.1:1.

When about 0.0007 moles of antiomy pentachloride was added to the reaction mixture, it was found that 24.8% of the di-n-butyl sulfide was converted to di-n-butyl sulfoxide after the heating period. This corresponds to an increase of about 20% over the control run results. The molar ratio of antimony pentachloride to organic sulfide was about 0.2:1.

The runs employing the metal promoters or graphite in combination with hydrochloric acid demonstrate that the yields of sulfoxide from the organic sulfide are increased compared to the yield obtained in the presence of hydrochloric acid alone.

EXAMPLE II

A series of reactions was conducted employing 20 ml portions of a stock solution consisting of 50 ml (0.290 moles) di-n-butyl sulfide, 120 ml (1.69 moles) dimethyl sulfoxide, 600 ml (10.3 moles) absolute ethanol and 15 g (0.104 moles) dibenzothiophene as a standard as before. In each run a different amount of 12 molar hydrochloric acid was added. While under a nitrogen flush, each mixture was heated to about 74° C (165° F) in about 13 minutes and maintained at that temperature. Aliquots were withdrawn at 1, 2.5 and 5.0 minutes, the vessel containing the aliquots were cooled in a wet ice bath and then the aliquots were analyzed. The results are presented in Table 1.

Table 1

| Butyl Sulfide Disappearance vs. Hydrochloric Acid Concentration | | |
|---|---|---|
| Run No. | Moles HCl Per Mole n-Butyl Sulfide | Disappearance n-Butyl Sulfide Moles Liter (1 min.) |
| 1 | 0.16 | no reaction detected at 30 seconds |
| 2 | 0.24 | 0.053 |
| 3 | 0.32 | 0.141 |
| 4 | 0.48 | 0.239 |
| 5 | 0.56 | 0.246 |
| 6 | 0.80 | 0.697 |
| 7 | 0.96 | 0.710 |
| 8 | 1.12 | 1.09 |
| 9 | 1.28 | 1.29 |
| 10 | 1.44 | 1.34 |
| 11 | 1.68 | 1.51 |
| 12 | 2.0 | 1.56 |

The disappearance of n-butyl sulfide rises almost linearly as the molar ratio of hydrochloric acid to n-butyl sulfide increases from about 0.3 to about 1.5. Below a molar ratio of about 0.3, the reaction proceeds very slowly. At molar ratios greater than about 1.5, other reactions begin to occur which result in a reduced yield of the sulfoxide.

These data show that hydrochloric acid appears to behave somewhat as a reactant rather than as a catalyst as reported by Hall and Bargar.

EXAMPLE III

A mixture consisting of 8.5 ml (0.049 moles) di-n-butyl sulfide, 10.5 ml (0.15 moles) dimethyl sulfoxide, 0.35 g of 18 molar sulfuric acid (equivalent to about 0.003 moles $H_2SO_4$) and 0.002 moles of zinc chloride was heated from room temperature to about 230° F in about 30 miuntes and from about 230° F to about 350° F (110°-177° C) over a period of about 2 hours in a stream of nitrogen. Analysis of the reaction mixture by GLC revealed a 95% conversion of the di-n-butyl sulfide with a 78% selectivity to di-n-butyl sulfoxide. The molar ratio of dimethyl sulfoxide to the organic sulfide was about 3.1:1. The molar ratio of sulfuric acid to organic sulfide was about 0.06:1 and the molar ratio of organic sulfide to zinc chloride was about 24:1.

A mixture like above, except with no zinc chloride present, was heated in a stream of nitrogen from room temperature to about 320° F in 40 minutes and then from about 320° to about 350° F (160°-177° C) over a period of about 2 ½ hours. Analysis of the reaction mixture revealed that only about 1% of the di-n-butyl sulfide had been converted to di-n-butyl sulfoxide.

This example demonstrates that when a hydrocarbyl sulfoxide and an organic sulfide are reacted in the presence of sulfuric acid, the presence of a suitable metal promoter provides an improved yield of the sulfoxide derived from the organic sulfide.

EXAMPLE IV

A mixture consisting of 8.8 ml (0.051 moles) di-n-butyl sulfide, 10 ml (0.141 moles) dimethyl sulfoxide and 0.002 moles of zinc chloride was heated from room temeperature to about 285° F (141° C) in about 15 minutes in a stream of nitrogen. The mixture was maintained at a temperature in the range of about 290° to about 350° F (143°-177° C) for about 6 ½ hours in a nitrogen atmosphere, then a sample was taken for analysis. The results indicated that di-n-butyl sulfoxide was not formed. The molar ratio of dimethyl sulfoxide to organic sulfide was about 2.8:1. The molar ratio of organic sulfide to zinc chlroide was about 25:1.

The remaining reaction mixture was cooled to room temperature and 0.27 g of 15 molar orthophosphoric acid (equivalent to about 0.002 moles H₃PO₄ added. The mixture was heated in a stream of nitrogen to 350° F and maintained at about that temperature for about 5 hours. A sample of the reaction mixture was taken and analyzed. The results indicated that about 50% of the di-n-butyl sulfide had been converted to di-n-butyl sulfoxide. The molar ratio of phosphoric acid to organic sulfide was about 0.06:1.

In another run, a mixture consisting of 8.5 ml (0.049 moles) di-n-butyl sulfide, 10.5 ml (0.148 moles) dimethyl sulfoxide and 0.36 g of 15 molar orthophosphoric acid (equivalent to about 0.003 moles H₃PO₄) was heated in a stream of nitrogen from room temperature to about 340° F (171° C) in 30 minutes. The reaction mixture was maintained at about 340° F for about 5½ hours in the nitrogen stream and a sample taken for analysis. The results indicated no formation of di-n-butyl sulfoxide. The molar ratio of dimethyl sulfoxide to organic sulfide was about 3:1. The molar ratio of phosphoric acid to organic sulfide was about 0.08:1.

This example demonstrates that neither a metal halide nor a protonic acid alone is effective in catalyzing the reaction between a hydrocarbyl sulfoxide and an organic sulfide under the reaction conditions employed. When the combination is employed, however, good yields of the sulfoxide derived from the organic sulfide are observed.

EXAMPLE V

A stock solution was prepared by mixing 293 ml (5.02 moles) absolute ethanol, 77 ml (1.08 moles) dimethyl sulfoxide, 23 ml (0.196 moles) methylphenyl sulfide and 16 ml (0.090 moles) phenanthrene as an internal standard. A 23 ml portion of the stock solution was mixed with 0.004 moles of 12 molar hydrochloric acid and 0.002 moles gallium trichloride. The mixture was heated in a stream of nitrogen to about 180° F (82° C) and maintained at that temperature for 1¼ hours. A sample of the mixture was analyzed and no disappearance of methylphenyl sulfide was noted.

The molar ratio of the sulfoxide to the organic sulfide was about 5.5:1. The molar ratio of hydrogen chloride to organic sulfide was about 0.4:1. The number of moles diluent employed was about 3.9 times the sum of the moles of sulfoxide and sulfide employed.

The results demonstrate that the combination of hydrochloric acid and gallium trichloride was not an effective catalyst system for converting methyl phenyl sulfide to the corresponding sulfoxide.

EXAMPLE VI

A stock solution was prepared containing 38.58 wt. % absolute ethanol (5.02 moles, 183 ml), 14.47 wt. % methylphenyl sulfide (0.44 moles, 52 ml), 45.96 wt. % dimethylsulfoxide (2.2 moles, 157 ml) and 0.99 wt. % phenanthrene (0.0208 moles, 4 ml) as an internal standard. A 20 ml portion of the stock solution was admixed with about 0.35 g of 12 molar hydrochloric acid (equivalent to about 0.004 moles hydrogen chloride) and about 0.0007 moles of antimony pentachloride. The mixture was heated under a nitrogen atmosphere for about 20 minutes at a temperature averaging about 178° C (358° F). An aliquot was withdrawn from the reaction mixture, cooled in a wet ice bath and analyzed by GLC. The results showed 80% conversion of methylphenyl sulfide to methylphenyl sulfoxide. No other products were detected.

The molar ratio of hydrogen chloride to organic sulfide was about 0.2:1. The molar ratio of dimethylsulfoxide to the organic sulfide was about 5:1. The number of moles diluent employed was about 1.2 times the sum of the moles sulfide and dimethylsulfoxide employed.

The results demonstrate that the combination of antimony pentachloride and hydrochloric acid provides a catalyst system that is effective in the conversion of methylphenyl sulfide to methylphenyl sulfoxide.

EXAMPLE VII

A sample of cat cracked gasoline was fractionated and cut at 121° C (250° F). The light end fraction (48 wt. % of the sample) was analyzed and found to contain 0.03 wt. % sulfur. A reactor was charged with 44.3 g of the light end fraction, 3.4 g (0.044 moles) dimethyl sulfoxide and 0.3 g (0.025 moles) powdered graphite and capped. Then a stream of 9.4 wt. % anhydrous HCl and 90.6 wt. % nitrogen was bubbled through the gasoline mixture for about 2.5 minutes at the rate of about 30 ml/minute. The calculated amount of HCl added was 0.00042 moles. The mixture was heated up to 108° C (226° F) over a period of about 1 hour and then cooled in wet ice. The resulting product was extracted first with 20 ml of a 1 wt. % sodium bicarbonate solution to remove HCl and then with four 20 ml portions of distilled water to remove the sulfoxides. The treated gasoline was dried and analyzed for sulfur. It was found that the sulfur content of the topped gasoline sample was reduced 33 wt. % by the treatment.

The results demonstrate that some reduction in the sulfur content of gasoline can be achieved by treating it according to the teachings of this invention.

From the foregoing description and examples, one skilled in the art can easily ascertain the essential characteristics of this invention and without departing from the spirit and scope thereof, can make various changes and modifications of the invention to adapt it to various usages and conditions. Consequently, such changes and modifications are properly, equitably, and intended to be, within the full range of equivalence of the following claims.

I claim:

1. A process for preparing an organic sulfoxide comprising reacting at least one organic sulfide of the formula

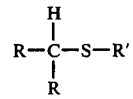

wherein each R is individually selected from the group consisting of hydrogen radicals, hydrocarbon radicals and hydrocarbyl radicals substituted with groups which don't interfere with the reaction or wherein the two R groups are combined to form a hydrocarbyl carbocyclic ring or a carbocyclic ring substituted with groups which don't interfere with the reaction, and wherein R' is selected from the group consisting of hydrocarbyl radicals and hydrocarbyl radicals substituted with groups which don't interfere with the reaction, with at least one hydrocarbyl sulfoxide of the formula

wherein each A is individually selected from the same or different alkyl radical having from 1 to 12 carbon atoms or wherein two such A alkyl groups are combined by a bond to form a sulfur-containing cyclic ring containing at least 4 carbons in the cyclic ring, in the presence of a reaction promoting amount of at least one protonic acid and at least one chloride containing-metal promoter selected from covalent metal chlorides capable of forming complex chloride coordination compounds or noncovalent metal chlorides or chloroplatinic acid, under suitable reaction conditions to obtain at least one organic sulfoxide corresponding to said at least one organic sulfide.

2. A process according to claim 1 wherein

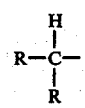

and — R' each contain 1 to 12 carbon atoms,

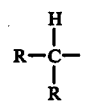

is selected from the group consisting of alkyl, cycloalkyl, and aralkyl radicals, and — R' is selected from the group consisting of alkyl, cycloalkyl, aralkyl, alkaryl, and aryl radicals.

3. A process according to claim 2 wherein the molar ratio of said organic sulfoxide to said organic sulfide is in the range of about 500:1 to about 1:10, wherein the amount of protonic acid per mole of organic sulfide is such that it will provide a hydrogen ion concentration in the range of an amount about equivalent to the hydrogen ion concentration provided by 0.05 mole of hydrogen chloride to an amount about equivalent to the hydrogen ion concentration provided by 2.5 moles of hydrogen chloride, and wherein the moles of acid chloride-containing metal promoter per mole of organic sulfide is in the range of about 0.0001/1 to about 1/1.

4. A process according to claim 3 wherein said protonic acid is selected from the group consisting of phosphoric acid and sulfuric acid.

5. A process according to claim 4 wherein said reaction is conducted at a temperature in the range of about 18° to about 180° C.

6. A process according to claim 5 wherein said reaction is conducted in an organic liquid diluent that does not have a significant adverse effect on the reaction.

7. A process according to claim 6 wherein said diluent is selected from one or more saturated aliphatic monohydric alcohols having from 1 to 8 carbon atoms.

8. A process according to claim 7 wherein said chloride-containing metal promoter is selected from the group consisting of lead chloride, zinc chloride, iron chloride, sodium chloride, lithium chloride, calcium chloride, antimony pentachloride, cadmium chloride, chloroplatinic acid, or mixtures thereof.

9. A process for preparing an organic sulfoxide comprising reacting at least one organic sulfide of the formula

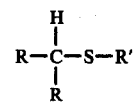

wherein each R is individually selected from the group consisting of hydrogen radicals, hydrocarbon radicals and hydrocarbyl radicals substituted with groups which don't interfere with the reaction or wherein the two R groups are combined to form a hydrocarbyl carbocyclic ring or a carbocyclic ring substituted with groups which don't interfere with the reaction, and wherein R' is selected from the group consisting of hydrocarbyl radicals and hydrocarbyl radicals substituted with groups which don't interfere with the reaction, with at least one hydrocarbyl sulfoxide of the formula

wherein each A is individually selected from the same or different alkyl radical having from 1 to 12 carbon atoms or wherein two such A alkyl groups are combined by a bond to form a sulfur-containing cyclic ring containing at least 4 carbons in the cyclic ring, in the presence of a reaction promoting amount of hydrogen chloride and at least one promoter selected from the group consisting of graphite, covalent metal halide capable of forming coordination compounds, chloroplatinic acid, and noncovalent metal halides.

10. A process according to claim 9 wherein $$R-\underset{R}{\overset{H}{\underset{|}{C}}}-$$

and — R' each contain 1 to 12 carbon atoms, $$R-\underset{R}{\overset{H}{\underset{|}{C}}}-$$

is selected from the group consisting of alkyl, cycloalkyl, and aralkyl radicals, and — R' is selected from the group consisting of alkyl, cycloalkyl, aralkyl, alkaryl, and aryl radicals.

11. A process according to claim 10 wherein the molar ratio of said organic sulfoxide to said organic sulfide is in the range of about 500:1 to about 1:10, wherein the molar ratio of hydrogen chloride to organic sulfide is in the range of about 0.05/1 to about 2.5/1, and wherein the mole ratio of said promoter to said organic sulfide is in the range of about 0.0001/1 to about 1/1.

12. A process according to claim 11 wherein said reaction is conducted at a temperature in the range of about 18° to about 180° C.

13. A process according to claim 12 wherein said reaction is conducted in an organic liquid diluent that does not have a significant adverse effect on the reaction.

14. A process according to claim 13 wherein said diluent is selected from one or more saturated aliphatic monohydric alcohols having from 1 to 8 carbon atoms.

15. A process according to claim 14 wherein said promoter is graphite.

16. A process according to claim 14 wherein said promoter is chloroplatinic acid.

17. A process according to claim 14 wherein said promoter is zinc chloride.

18. A process according to claim 14 wherein said promoter is ferric chloride.

19. A process according to claim 14 wherein said promoter is antimony pentachloride.

20. A process according to claim 14 wherein said promoter is lead dichloride.

21. A process according to claim 14 wherein said promoter is copper dichloride.

22. A process according to claim 14 wherein said promoter is bismuth trichloride.

23. A process according to claim 14 wherein said promoter is mercury dichloride.

24. A process for preparing an organic sulfoxide comprising reacting at least one organic sulfide of the formula

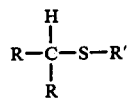

wherein each R is individually selected from the group consisting of hydrogen radicals, hydrocarbon raidcals and hydrocarbyl radicals substituted with groups which don't interfere with the reaction or wherein the two R groups are combined to form a hydrocarbyl carbocyclic ring or a carbocyclic ring substituted with groups which don't interfere with the reaction, and wherein R' is selected from the group consisting of hydrocarbyl radicals and hydrocarbyl radicals substituted with groups which don't interfere with the reaction, with at least one hydrocarbyl sulfoxide of the formula

wherein each A is individually selected from the same or different alkyl radical having from 1 to 12 carbon atoms or wherein two such A alkyl groups are combined by a bond to form a sulfur-containing cyclic ring containing at least 4 carbons in the cyclic ring, in the presence of a reaction promoting amount of hydrogen chloride and graphite.

* * * * *

UNITED STATES PATENT AND TRADEMARK OFFICE
CERTIFICATE OF CORRECTION

PATENT NO. : 4,113,784
DATED : September 12, 1978
INVENTOR(S) : William G. Billings It is certified that error appears in the above-identified patent and that said Letters Patent are hereby corrected as shown below:

Column 9, line 12, delete "chloride contain-ing" and insert therefor --- chloride-containing ---;

Column 9, line 47, delete "acid" and insert therefor --- said ---; and

Column 12, line 8, delete "raidcals" and insert therefor --- radicals ---.

Signed and Sealed this

Sixth Day of February 1979

[SEAL]

Attest:

RUTH C. MASON
Attesting Officer

DONALD W. BANNER
Commissioner of Patents and Trademarks